United States Patent
Jenkins et al.

[11] Patent Number: 6,126,614
[45] Date of Patent: Oct. 3, 2000

[54] APPARATUS AND METHOD FOR ANALYSIS OF EAR PATHOLOGIES BY DETECTING FLUID IN THE EAR, MEASURING BODY TEMPERATURE AND/OR DETERMINING A CHARACTERISTIC OF A FLUID

[75] Inventors: Geoffrey Jenkins, Wellesley; Sandra Kimball, Boston; David Kunen, Wayland, all of Mass.

[73] Assignee: MDI Instruments, Inc., Woburn, Mass.

[21] Appl. No.: 09/228,967

[22] Filed: Jan. 12, 1999

Related U.S. Application Data

[63] Continuation of application No. 09/177,924, Oct. 23, 1998, and application No. 09/006,543, Jan. 12, 1998.

[51] Int. Cl.$^7$ ............................................. A61B 5/00
[52] U.S. Cl. ........................ 600/549; 600/559; 600/573
[58] Field of Search .................................. 600/549, 559, 600/573, 584

[56] References Cited

U.S. PATENT DOCUMENTS

| | | | |
|---|---|---|---|
| 5,820,264 | 10/1998 | Tsao et al. | 600/549 |
| 5,833,367 | 11/1998 | Cheslock et al. | 600/549 |
| 5,833,626 | 11/1998 | Leysieffer | 600/559 |
| 5,868,682 | 2/1999 | Combs et al. | 600/559 |
| 5,873,833 | 2/1999 | Pompei | 600/549 |

*Primary Examiner*—Max Hindenburg
*Assistant Examiner*—Pamela L. Wingood

[57] ABSTRACT

An improved indication of a condition of an ear of a subject, such as a human or other mammal, is provided by combining two or more measurements such as body temperature, detection of fluid in the ear (for example by acoustic reflectance), and/or a characteristic of any fluid in the ear. Results of any two of these measurements may be combined to provide improved diagnostic information. The combination of measured body temperature and a determined likelihood that fluid is present in the ear provides improved diagnostic information regarding the risk of an ear infection. In particular, if a subject has an elevated body temperature and the likelihood is high that fluid is present in the ear, an indication of a risk of ear infection may be provided by the device. The presence of fluid may be detected using acoustic reflectometry, tympanometry, pneumatic otoscopy, otoacoustic emissions or other mechanism. If temperature is measured in the ear, for example by using radiation thermometry, the combined instrumentation may be used to improve alignment between the device and the tympanic membrane, thus improving the accuracy of both temperature measurement and fluid detection. Chemical sensing of characteristics of any fluid in the ear may be combined with the detection of fluid or measurement of body temperature, or both, to provide improved diagnosis of ear pathologies. Chemical sensing determines a characteristic of the fluid, such as whether a bacterium or a virus is present. The device may provide diagnostic information from sensed characteristics of the fluid, measured likelihood that fluid is present in the ear and/or measured body temperature to indicate the risk of an ear infection. For example, the device may determine whether any fluid present is infected, and/or may identify bacteria in the fluid.

52 Claims, 11 Drawing Sheets

| | TEMP <99° | TEMP 99° - 100° | TEMP >100° |
|---|---|---|---|
| 506 — S.G. ANGLE >95° | WELL ᵃ | LOW FLUID NO FLUID ᵇ | HI TEMP NO FLUID ᶜ |
| 508 — S.G. ANGLE 70° - 95° | OME ᵈ | AOM ᵉ | AOM ᶠ |
| 510 — S.G. ANGLE <70° | OME ᵍ | AOM ʰ | AOM ⁱ |

(columns labeled 500, 502, 504)

FIG. 14

| EAR INFECTION | AOM |
|---|---|
| HI | f, h, i |
| MOD | e, g |
| LOW | a, b, c, d |

FIG. 15

| FLUID | OME |
|---|---|
| HI | g, h, i |
| MOD | d, e, f |
| LOW | a, b, c |

FIG. 16

| ANGLE | BACTERIA/ VIRUSES PRESENT | BACTERIA/ VIRUSES ABSENT |
|---|---|---|
| >95° | AOM LOW | OME LOW |
| 70° - 95° | AOM MODERATE | OME MODERATE |
| <70° | AOM HIGH | OME HIGH |

FIG. 17

| TEMPERATURE | BACTERIA/ VIRUSES PRESENT | BACTERIA/ VIRUSES ABSENT |
|---|---|---|
| >100° | AOM HIGH | OME MODERATE |
| 99°- 100° | AOM MODERATE | OME MODERATE |
| <99° | AOM MODERATE | OME LOW |

FIG. 18A
BACTERIA / VIRUSES PRESENT

| ANGLE/ TEMPERATURE | <99° | 99° - 100° | >100° |
|---|---|---|---|
| >95° | AOM LOW | AOM MODERATE | AOM MODERATE |
| 70° - 95° | AOM HIGH | AOM HIGH | AOM HIGH |
| <70° | AOM HIGH | AOM HIGH | AOM HIGH |

FIG. 18B
BACTERIA / VIRUSES ABSENT

| ANGLE/ TEMPERATURE | <99° | 99° - 100° | >100° |
|---|---|---|---|
| >95° | AOM LOW | AOM LOW | AOM LOW |
| 70° - 95° | AOM MODERATE | AOM MODERATE | AOM MODERATE |
| <70° | AOM HIGH | AOM HIGH | AOM HIGH |

APPARATUS AND METHOD FOR ANALYSIS OF EAR PATHOLOGIES BY DETECTING FLUID IN THE EAR, MEASURING BODY TEMPERATURE AND/OR DETERMINING A CHARACTERISTIC OF A FLUID

CROSS-REFERENCE TO RELATED APPLICATIONS

This application is a continuing application of U.S. patent application Ser. No. 09/177,924, filed Oct. 23, 1998, now pending and a continuing application of U.S. patent application Ser. No. 09/006,543, filed Jan. 12, 1998, now pending.

BACKGROUND

One device that has become generally accepted and is commonly used by physicians and other health care professionals is known as a radiation thermometer, or infrared thermometer. Such devices are commercially available from Thermoscan, Inc. of San Diego, Calif. Devices of this type are described, for example, in U.S. Pat. Nos. 5,368,038 (Fraden), 4,797,840 (Fraden), 4,479,931 (Mooradian), 5,127,742 (Fraden), 5,178,464 (Fraden), 5,626,147 (Lackey), 4,895,164 (Wood), and 5,199,436 (Pompei). A radiation thermometer noninvasively detects thermal radiation from the tympanic membrane in order to determine the body temperature of the patient. A temperature reading made with this device may vary depending on the angle and depth of placement of the tip of the device with respect to the ear canal. In particular, the geometric relationship between the sensor and the tympanic membrane influences the ultimate reading by the sensor in operation. The field of view of the device when detecting thermal radiation also affects the temperature reading. The technology described in U.S. Pat. No. 5,626,147 (Lackey) seeks to solve these problems by using a sensor geometry which has wide and narrow fields of view and a look-up table with corrective values to provide an output indicative of the body temperature.

Another device that is used for diagnosis of ear pathologies is known as an acoustic reflectometer. Such devices are commercially available from MDI Instruments, Inc. of Woburn, Mass. under the trademarks "EARCHECK" and "EARCHECK PRO." Devices of this type are described, for example, in U.S. Pat. Nos. 4,601,295 (Teele), 4,459,966 (Teele), and 5,699,809 (Combs et al.), all of which are assigned to MDI Instruments, Inc. U.S. Pat. Nos. 5,594,174 (Keefe) and 5,651,371 (Keefe) also describe a device for measuring acoustic reflectance in a manner that permits the incident and reflected acoustic signals to be separately measured. An acoustic reflectometer measures sound waves emitted from the ear in response to a stimulus applied to the ear. The measured reflectance may be analyzed to determine the likelihood that fluid is present in the middle ear. Without correction or appropriate signal analysis, measurements made using an acoustic reflectometer also may be affected by line of sight from the tip of the device to the tympanic membrane. Although U.S. Pat. No. 5,699,809 (Combs et al.) describes a device in which the output is substantially independent of the line of sight, the device primarily determines the likelihood that fluid is present in the ear. However, in the detection of acute otitis media (AOM), otitis media with effusion (OME) or severe ear infection, the presence of fluid is only one factor in a diagnosis.

SUMMARY

An improved indication of a condition of an ear of a subject, such as a human or other mammal, is provided by combining two or more measurements such as body temperature, detection of fluid in the ear (for example by acoustic reflectance), and/or a characteristic of any fluid in the ear. Results of any two of these measurements may be combined to provide improved diagnostic information.

The combination of measured body temperature and a determined likelihood that fluid is present in the ear provides improved diagnostic information regarding the risk of an ear infection. In particular, if a subject has an elevated body temperature and the likelihood is high that fluid is present in the ear, an indication of a risk of ear infection may be provided by the device. The presence of fluid may be detected using acoustic reflectometry, tympanometry, pneumatic otoscopy, otoacoustic emissions or other mechanism. If temperature is measured in the ear, for example by using radiation thermometry, the combined instrumentation may be used to improve alignment between the device and the tympanic membrane, thus improving the accuracy of both temperature measurement and fluid detection.

Chemical sensing of characteristics of any fluid in the ear may be combined with the detection of fluid or measurement of body temperature, or both, to provide improved diagnosis of ear pathologies. Chemical sensing determines a characteristic of the fluid, such as whether a bacterium or a virus is present. The device may provide diagnostic information from sensed characteristics of the fluid, measured likelihood that fluid is present in the ear and/or measured body temperature to indicate the risk of an ear infection. For example, the device may determine whether any fluid present is infected, and/or may identify bacteria in the fluid.

Accordingly, in one aspect a medical instrument for analyzing an ear of a subject includes a temperature sensor for measuring body temperature of the subject and providing a first signal indicative thereof. A fluid detector detects presence of fluid in the ear to provide a second signal indicative thereof. A controller is connected to the temperature sensor and the fluid detector to control acquisition of the first and second signals. A processor may be connected to receive the first and second signals for determining, using the measured body temperature and the detected presence of fluid in the ear, an indication of a condition of the ear of the subject. An array of chemical sensors responsive to a characteristic of the fluid, may be used to provide a third signal indicative thereof. The controller further would be connected to the array of chemical sensors to control acquisition of the third signal.

In another aspect, a device for providing an indication of a condition of an ear of a subject has a first input for receiving a first signal indicative of a measured body temperature of the subject. A second input receives a second signal indicative of a likelihood of presence of fluid in the ear of the subject. A processor is connected to receive the first and second inputs for determining, using the measured body temperature and the likelihood of presence of fluid in the ear, the indication of the condition of the ear of the subject. A third input may be used to receive a third signal indicative of a determined characteristic of any fluid in the ear of the subject. The processor would be connected to receive the third input to determine the indication of the condition of the ear of the subject further using the determined characteristic of any fluid in the ear of the subject.

In another aspect, a medical instrument for analyzing an ear of a subject includes an array of chemical sensors responsive to a characteristic of any fluid in the ear to provide a first signal indicative thereof. A fluid detector detects presence of fluid in the ear to provide a second signal indicative thereof. A controller is connected to the array of chemical sensors and the fluid detector to control acquisition of the first and second signals.

In another aspect, a medical instrument for analyzing an ear of a subject includes an array of chemical sensors responsive to a characteristic of the fluid to provide a first signal indicative thereof. A temperature sensor measures body temperature of the subject and providing a second signal indicative thereof. A controller is connected to the array of chemical sensors and the temperature sensor to control acquisition of the first and second signals.

Similarly, another aspect is a process for analyzing an ear that includes measuring body temperature of the subject and detecting fluid in the ear. Another aspect is a process for analyzing an ear that includes chemical sensing of a characteristic of a fluid and detecting fluid in the ear. Another aspect is a process for analyzing an ear that includes chemical sensing of a characteristic of fluid in the ear and measuring body temperature of the subject. Another aspect is a process for analyzing an ear that includes chemical sensing of a characteristic of a fluid in the ear, measuring body temperature of the subject, and detecting fluid in the ear.

In various embodiments, fluid in the ear may be detected using an acoustic transducer for generating acoustic energy in the ear. A microphone detects acoustic energy from the ear. An acoustic reflectometer, comprising an acoustic transducer for generating acoustic waves at a plurality of frequencies and a microphone for receiving acoustic signals reflected from the ear, may be used to provide an output signal. A tympanometer, pneumatic otoscope, otoacoustic emissions or other mechanism also may be used to detect fluid.

In various embodiments, body temperature may be determined using a radiation sensor for detecting thermal radiation from the ear and providing a signal indicative thereof. Another mechanism, such as a thermistor or other temperature sensitive device, also may be used to measure body temperature, such as in the mouth, rectum or on the surface of the skin. A measured body temperature may be manually entered into a device.

The various combinations of measurements provide an indication of a risk of an ear infection. In particular, if fluid is detected in the ear and the subject has an elevated body temperature, an indication of a risk of an ear infection may be provided. If a bacterium or virus or other negative characteristic of fluid are detected in the ear, an indication of a risk of an ear infection may be provided. If a bacterium or virus or other negative characteristic are detected in the ear and the subject has an elevated body temperature, an indication of a risk of an ear infection may be provided. If a bacterium or virus or other negative characteristic and fluid are detected in the ear, and the subject has an elevated body temperature, an indication of a risk of an ear infection may be provided.

DETAILED DESCRIPTION

The following detailed description should be read in conjunction with the attached drawings in which similar reference numbers indicate similar structures. All references cited herein are hereby incorporated by reference.

An indication of a condition of ear can be provided by using two or more of the following: measured body temperature, determined likelihood of presence of fluid in the ear, and/or any determined characteristic of any fluid in the ear. The characteristic of the fluid may indicate whether the fluid is infected. In particular, the bacterial and viral composition of the fluid may be determined. Body temperature may be measured using an infrared sensor, or thermistor or other temperature sensitive device, and may be measured through the ear, mouth, rectum or the surface of the skin or using any other conventional body temperature measurement. The likelihood that fluid is present in the middle of the ear may be determined, for example, by using acoustic reflectance, tympanometry, pneumatic otoscopy, otoacoustic emittance or other methods. If body temperature is measured through the ear, for example by using radiation thermometry, the temperature sensor may be used to align the device with the tympanic membrane, thus improving acoustic reflectance and temperature measurements. The combined measurements and the detected characteristic of the fluid, such as its bacterial and viral composition, may be used together to enhance diagnosis of ear conditions. In particular, if fluid is detected in the ear and the subject has an elevated body temperature, an indication of a risk of an ear infection may be provided. If bacteria and viruses and fluid are detected in the ear, an indication of a risk of an ear infection may be provided. If bacteria and viruses are detected in the ear and the subject has an elevated body temperature, an indication of a risk of an ear infection may be provided. If bacteria and viruses and fluid are detected in the ear, and the subject has an elevated body temperature, an indication of a risk of an ear infection may be provided.

Figure 1:
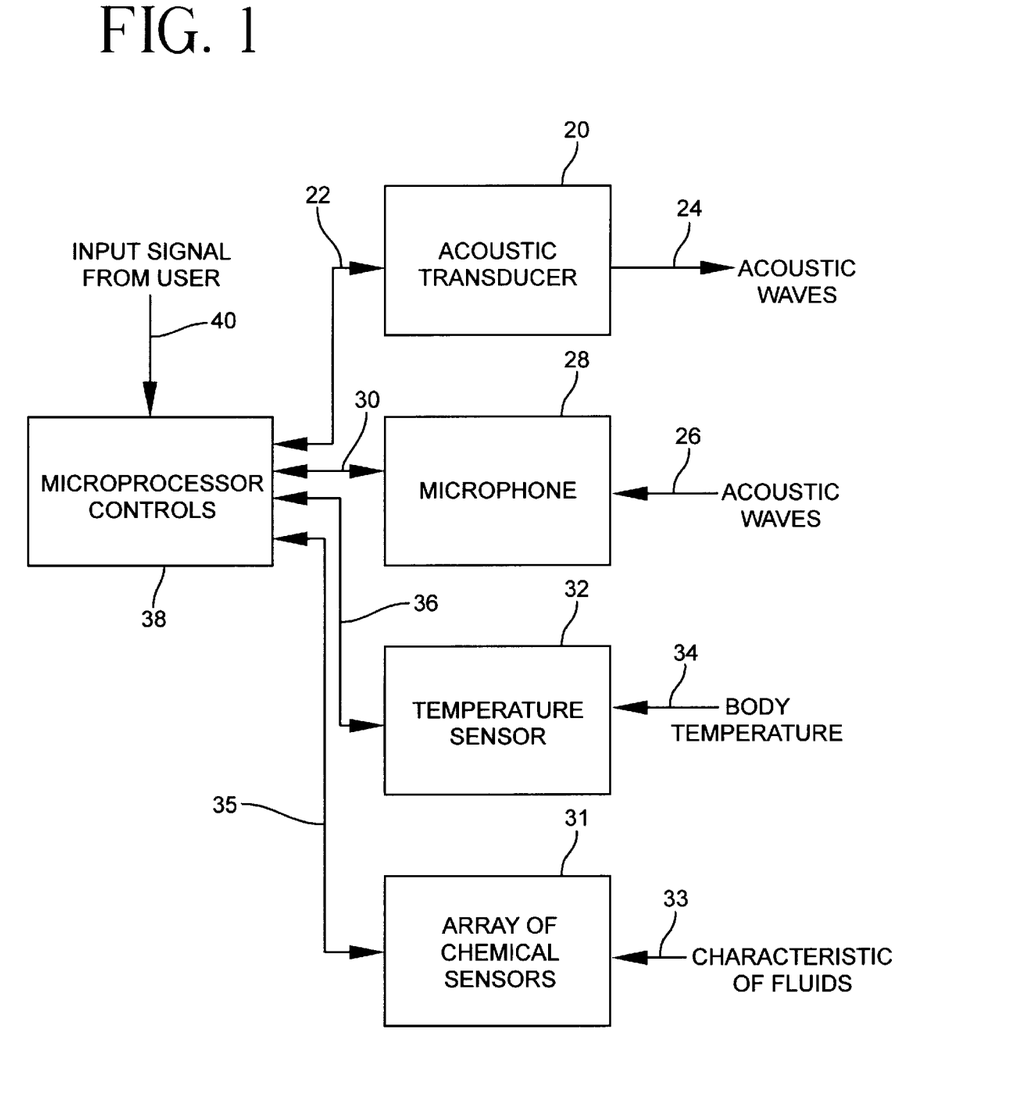
FIG. 1 is a block diagram of the electronic components of the combined array of chemical sensors, fluid detector and temperature sensor.

FIG. 1 illustrates a circuit diagram for a device that combines acoustic reflectometry for detecting fluid in the ear, a temperature sensor that senses temperature in the ear and chemical sensing of a characteristic of a fluid. The circuit includes an acoustic transducer 20 which, in response to inputs 22 from a microprocessor controller 38, emits acoustic waves 24 into, for example, the ear canal. These incident acoustic waves 24 and reflected acoustic waves 26 are received by a microphone 28. In some embodiments, it is possible to separate the reflected acoustic waves from the incident acoustic waves. The microphone 28 provides this measurement to the microprocessor controller 38 as indicated at 30. A temperature sensor 32 senses temperature 34 in the ear and provides a signal 36 to the microprocessor controller 38. An array of chemical sensors 31 detects a characteristic of the fluid 33 in the ear and provides signal 35 to the microprocessor controller. For example, the array of chemical sensors may detect the presence of specific bacteria and viruses.

The microprocessor controller 38 receives an input signal 40 from the user which indicates whether a reading should be taken. The microprocessor controller 38 then controls the acoustic transducer, microphone, temperature sensor, and array of chemical sensors to obtain data. The microprocessor controller 38 processes the data to provide results for display to the user, for example, according to the process described in FIG. 9 below.

A process for measuring acoustic reflectance of an ear will first be described in connection with FIGS. 2–5. Acoustic reflectometers are described in U.S. Pat. Nos. 4,459,966, 4,601,295, 5,594,174, 5,651,371, and PCT Application No. WO96/23293, cited above and U.S. patent application Ser. No. 09/006,543, filed Jan. 12, 1998, and U.S. patent application Ser. No. 09/012,695, filed Jan. 23, 1998, and PCT Application No. WO98/23205, published Jun. 4, 1998, and U.S. Pat. No. 5,699,809, issued Dec. 23, 1997, and hereby incorporated by reference. Other implementations also may be used.

Figure 2:
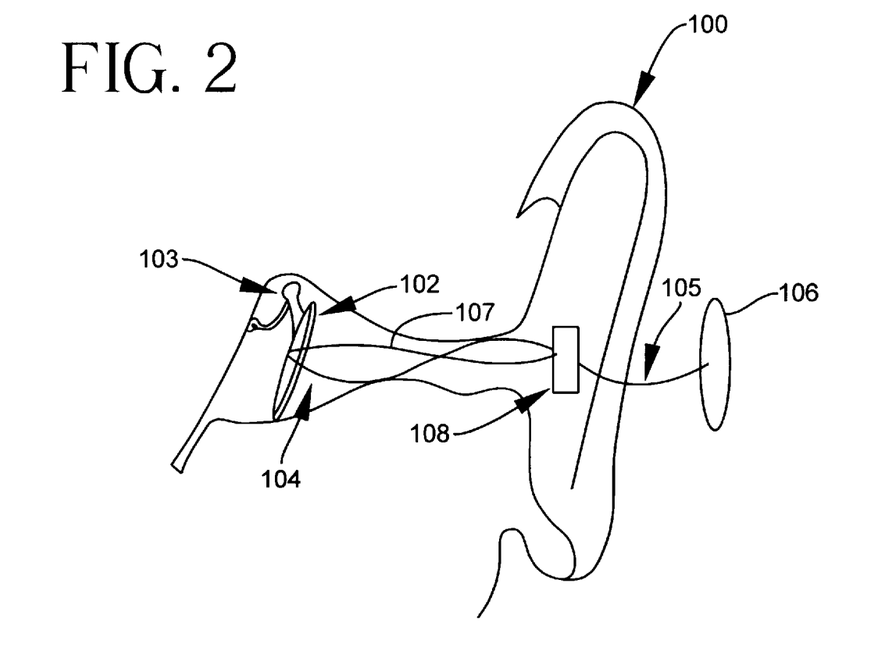
FIG. 2 is diagram illustrating acoustic reflectance of a healthy ear.

FIG. 2 shows a typical ear 100 having a tympanic membrane (an ear drum) 102, an ear canal 104, and middle ear 103. To measure acoustic reflectance, a low amplitude tone at a given frequency, indicated by line 105, is generated by an acoustic transducer, shown schematically at 106. The acoustic transducer generates sound waves for several frequencies, typically in the range of 500 Hertz to 20 kilohertz, or more particularly, 1.8 kilohertz to 4.4 kilohertz. The low amplitude sound wave enters the ear canal and is incident on the ear drum 102. This sound wave is absorbed in part and reflected in part by the ear structures, including the tympanic membrane, osicles, middle ear cleft and other components of the middle ear. The amplitude and phase of the reflected sound waves from these components are a function of the test frequency used and the complex acoustic impedance of the ear structures. In a healthy ear, some minimal reflection from the tympanic membrane and middle ear is expected. The complex acoustic impedance of the middle ear, in turn, depends strongly on the conditions within the middle ear, and in particular on whether there is an effusion, such as fluid or abnormal pressure, in the middle ear. The vibration of a normal ear drum absorbs approximately half of the incident waves, resulting in weak reflected waves indicated by a line 107. A microphone 108 receives both the incident wave 105, the reflected wave 107 and reflected waves from ear components and as a result obtains a vector sum of the values. In other embodiments, the reflected sound may be separated from the incident sound.

Figure 3:
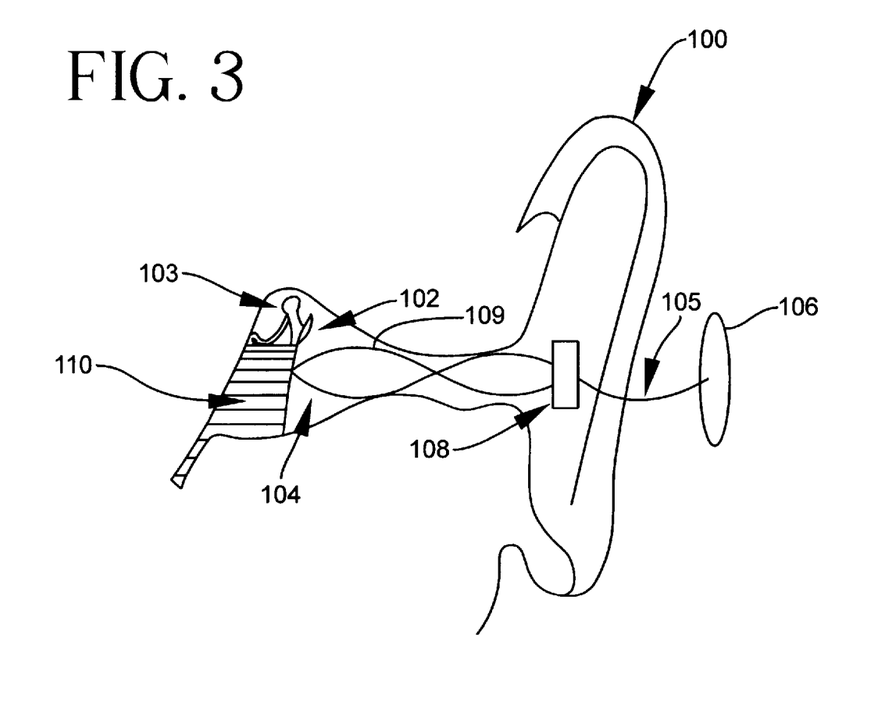
FIG. 3 illustrates acoustic reflectance and an ear having fluid behind the tympanic membrane.

Referring now to FIG. 3, an ear 100 is shown to have effusion 110. The middle ear effusion limits ear drum vibration, causing large reflected waves to have a larger amplitude as indicated at 109. The envelope of a vector sum of incident waves 105 and reflected waves 109, herein called an acoustic reflectance curve, has a null at the quarter wavelength points.

The shape of a region of the acoustic reflectance curve, defined by at least two points on the curve, is measured electronically to obtain an indicator of ear condition which is substantially independent of the line of sight between the sound source and the tympanic membrane. The indicator may be a measure of the rate of change of the acoustic reflectance with respect to a change in frequency on either or both sides of the null, around the null, of other regions of the curve or of the entire curve. The area around the null is where the curve has a significant negative slope, defining entry into the null, to a point just before the null, and after the null, where the curve has a significant positive slope, defining the exit of the null. The null typically occurs near the resonance frequency of the ear. The significance of this measurement will now be described.

As the sound wave incident to the tympanic membrane approaches a frequency where its quarter waves are coincident, the amplitude of the vector sum of the reflected sound waves and the incident sound waves approaches a null. Generally speaking, normally conducting ear drums without fluid or abnormal pressure in the middle ear demonstrate a relatively shallow acoustic null. Conversely, fluid or abnormal pressure in ears causes a stronger reflection and therefore a deeper acoustic null. The depth of this null is dependent, however, on the line of sight to the eardrum. It has been discovered, however, that the rate of change of the acoustic reflectance between the entry into the null and the exit from the null is steeper for ears having middle ear fluid or pressure than for healthy ears. It was further discovered that differences in this rate of change due to changes in line of sight have less of an impact on the indication of the presence of an effusion or abnormal pressure.

Eardruns that are free to vibrate with the incident sound wave (i.e., healthy) produce not only a less deep null but also a less steep slope at frequencies around the null and thus a larger spectral gradient angle. The restrained motion produces lower reflectance values relative to the null at nearby frequencies and therefore an apparent lower slope.

When the eardrum motion is restrained (i.e., the ear is not healthy), the slope around the null is steeper. Because acoustic reflectance is related to the complex acoustic impedance of the tympanic membrane, the measure of its rate of change with respect to frequency input is analogous to measuring the "Q" of an electrical circuit. Thus, restraining the ear drum results in both a higher acoustic impedance and a sharper "Q." The "Q" is relatively constant for a given impedance regardless of variations in the amount of energy incident because of line of sight limitations.

Figure 4:
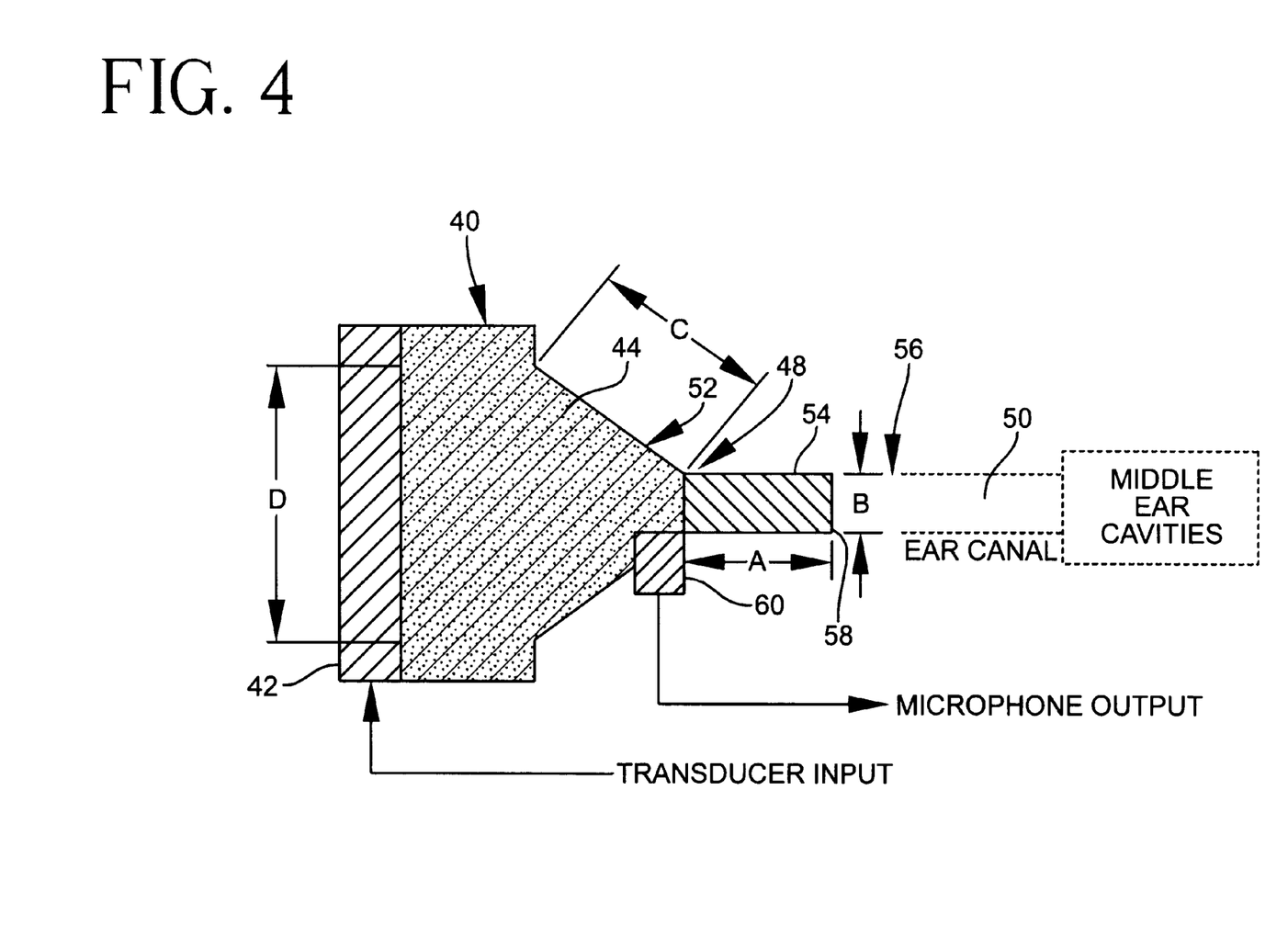
FIG. 4 is a diagram of test head that may be used for acoustic reflectance.

A device for one embodiment will now be described. FIG. 4 is a cross sectional diagram of a test head for an instrument in one embodiment. The test head 40 includes a transducer 42 that creates a sound field in sound cavity 44. Sound in the cavity 44 is channeled through probe 48 to the vicinity of the ear canal 50. The probe has a funnel-shaped section 52 and an optional linear section 54. The dimensions of section 54 may be chosen to match the dimensions of the typical ear canal under test. This section matches the impedance of the probe tip and the typical ear canal. For children's ears, length A of the linear portion 54 of the probe preferably is equal to approximately 1 cm and inner diameter B of the same section should be in the range of approximately 0.25 to 0.75 cm. Similarly, good results are obtained when length C along the side of funnel-shaped section 52 of the probe is about 5 cm and the approximate outer diameter D of the large end of the probe which is in contact with the sound cavity wall is approximately 7 cm. With appropriate compensation, tips with other exit diameters may be used. The probe extension does not need to be inserted into the ear canal. In practice, there may be a narrow gap 56 between the test head probe tip 58 and the entrance to the ear canal 50. Control of this gap may be facilitated by a response rubber spacer (not shown) attached at the end of probe tip 58.

The incident sound wave created by transducer 42 in the test head emanates from the test head at the tip 58 of the probe 48 and enters the ear canal 50. Thereafter, a portion of the incident wave is reflected by structures of the ear. Minimal reflection from a healthy ear can be suppressed by suitable selection of the inner probe tip diameter, e.g., by enlarging it to 1.0 cm for children.

Portions of the reflected waves enter at tip 58 into the hollow linear portion 54 of the test head. The microphone 60 is located within the test probe 48 at the junction of the linear portion of 54 and the funnel-shaped section 52. As a result, the microphone 60, in effect, measures the net sound pressure at this point; this net sound pressure is the vector sum of the incident and reflected signals. In order to reduce internal sound reflection and resonances within the test head, the sound cavity 44 may be filled with acoustic absorbing materials.

In other embodiments, a transfer function describing the acoustic characteristics of the ear may be determined and used as the basis for a diagnosis.

Figure 5:
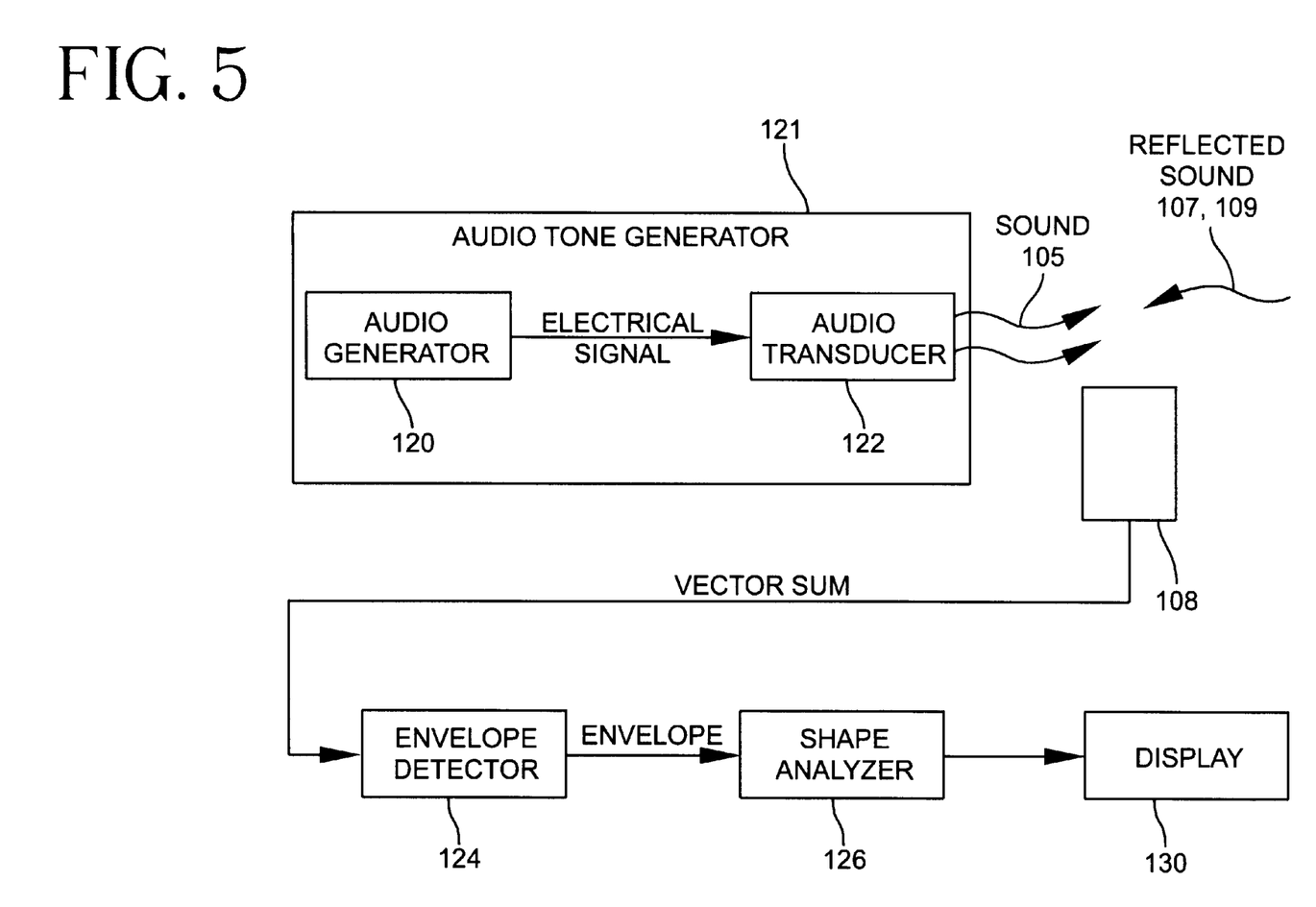
FIG. 5 is a block diagram describing an electronic circuit for measuring acoustic reflectance.

Having now described the general principles for measuring acoustic reflectance, and a suitable test head for use in an acoustic reflectometer, electronic circuitry suitable for an embodiment will now be described in connection with FIG. 5. FIG. 5 is a general block diagram of a device of one embodiment, including its electrical and mechanical components. The components of this circuit may be implemented using a microprocessor, except for the display, acoustic transducer and microphone. An analog implementation also may be made. In FIG. 5, an audio tone generator 121 includes an audio generator 120, which produces an electrical signal which is applied to an audio transducer 122 (such as transducer 42 in the test head of FIG. 4). The audio transducer, in response to the electrical signal, generates a low level acoustic sound wave (105 in FIGS. 2 and 3) which is applied to the outer ear canal. The audio transducer 122 may be an electronic earphone, electromagnetic earphone, or other type of transducer. The transducer may be a small loudspeaker such as used in high fidelity sound headsets.

A portion of the incident sound wave is reflected by ear structures as described above. In this embodiment, these reflected waves are summed with an incident wave by microphone 108 (such as microphone 60 of the test head of FIG. 4). The microphone may be a condenser microphone, an electrostatic microphone or other kind of microphone. In this embodiment, the signal output by the microphone represents the vector sum of the incident wave and the reflected sound waves, having a voltage which is inversely proportional to the amplitude of the reflected waves.

An envelope detector 124 converts the vector sum represented by the signal output by the microphone to an envelope signal represented by a voltage which varies with the frequency of the incident wave. The envelope detector 124 may be implemented as a peak value envelope detector, a root-mean square (RMS) voltage detector, or analog-to-digital converter, such as part of a suitably programmed microprocessor. In one embodiment described in more detail below, the envelope is detected using information about the frequency spectrum of the vector sum. The envelope so detected is called the acoustic reflectance curve.

A shape analyzer 126 measures the shape of a region of the acoustic reflectance curve to obtain an indicator of ear condition which is substantially independent of the line of sight from a sound source to the tympanic membrane. This information may be one or more measures of the shape of the envelope including a measure of the rate of change of acoustic reflectance with respect to a change in frequency around the null, on either side of the null or on a region of the curve or of the entire curve. This measure, for example, may be an angle, gradient, slope, width, or other measure of the shape of the acoustic reflectance curve determined in a manner to be described below. This information is then displayed in a suitable format by display section 130.

In FIG. 5, a memory (not shown) may be added to store results of processing of one acoustic reflectance curve. With such a memory, the circuit may be operated to perform automatically a number of tests sequentially on the ear. The best results for the sequence of tests may be kept and the others may be discarded. For example, the best results could be defined as the measurement of the shape of the acoustic reflectance curve having the deepest null value. In this manner, a user of the device may attempt to obtain the best result with minimal effort. The use of this memory is described below in more detail in connection with FIG. 9.

Fluid may be detected in the ear using methods other than acoustic reflectance. Such other methods include tympanometry, pneumatic otoscopy or otoacoustic emissions, and other techniques. Accordingly, the invention is not limited to the use of acoustic reflectance to detect fluid in the ear. In general, these technologies detect a response of the ear to sound, from which the presence of fluid may be determined.

Having now described how fluid may be detected in an ear, the temperature sensor will now be described. In one embodiment, the temperature sensor is implemented as a radiation sensor as shown in U.S. Pat. Nos. 5,626,147; 5,368,038; 5,199,436; 5,178,464; 5,127,742; 4,797,840; and 4,479,931, cited above and hereby incorporated by reference. Other embodiments of radiation sensors are known and also may be used. Using a radiation thermometer, body temperature is measured through the ear.

Body temperature also may be measured through the mouth or rectum or on the surface of the skin. Various kinds of temperature sensors may be used to measure body temperature, such as thermistors and other temperature sensitive electronic devices. From such devices, a signal indicative of the temperature may be read by a microprocessor. The device alternatively may permit a user to enter a measured body temperature.

One kind of radiation thermometer uses a sensor system that compensates for different ear canal placement geometries by creating an IR signal collected via both wide and narrow fields of view. By using IR information that is responsive to a wide field of view in conjunction with information from a narrow field of view, the errors in temperature reading occasioned by the vagaries in probe positioning in the ear can be compensated by appropriately programmed signal adjustment. Specifically, the signal processor integrated with the sensor weights the input from both sources and using a look-up table, applies corrective values to give an accurate and repeatable temperature measurement. This value also is indicative of alignment of the device with the ear.

Figure 6:
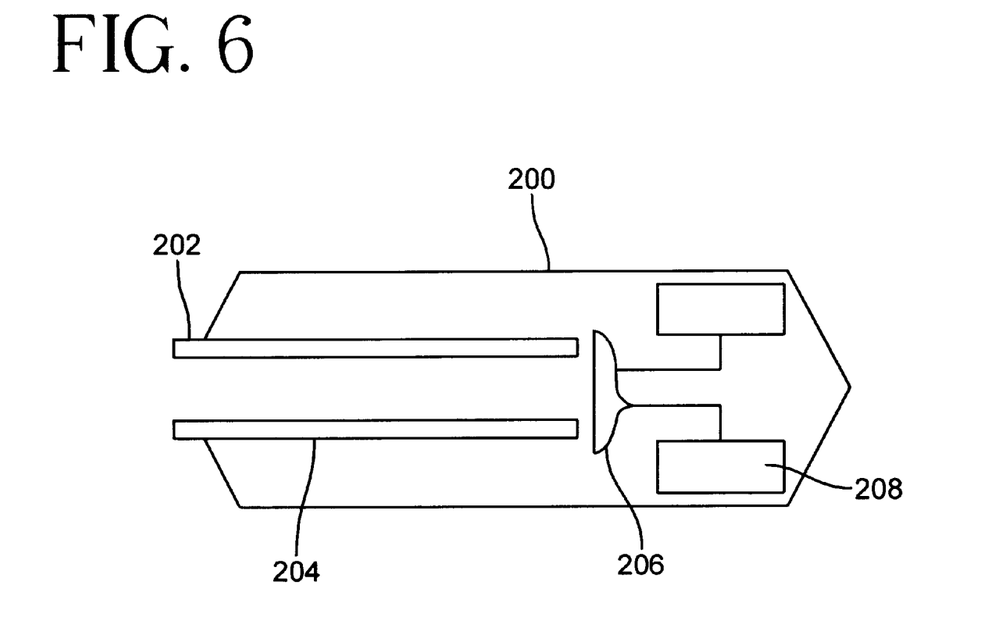
FIG. 6 is a diagram illustrating a radiation thermometer.

FIG. 6 provides a simplified diagram of elements in one embodiment of an IR thermometer. In this illustrative diagram, the thermometer device provides a housing 200 for the operative elements of the device. The housing has a terminus end at which an IR receiving opening 202 is positioned to feed incoming radiation to a wave guide 204. There are a variety of possible wave guides available for use that offer different performance characteristics such as distortion, ranging from smooth gold-plated tubes to fiber optic bundles. In functional terms, the wave guide is designed to collect and pass incoming radiation undisturbed to IR sensor 206. Again, there are several choices in sensor systems, including thermopile types and pyroelectric elements. In the embodiment to be described, the sensor is a pyroelectric sensor, which uses "matched pairs" to cancel out signal contributions intrinsic with the pyroelectric elements.

Continuing with FIG. 6, the sensor 206 is connected to processor 208 for converting the IR data into a high quality temperature reading as well be described in more detail below. The sensor design may be such that it provides signals for both wide and narrow fields of view. These signals are provided by creating two or more sensors, each reporting separately to the processor information on radiation.

Figure 7:
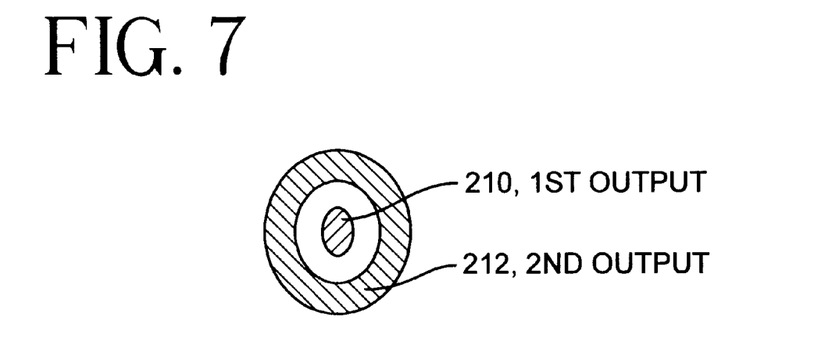
FIG. 7 is a diagram illustrating two sensors for use with radiation thermometry.

Such a sensor geometry is depicted in FIG. 7. More specifically, the sensor 206 of FIG. 5 is, in fact, two separate sensors, 210 and 212, each connected to the processor 208. The first sensor 210 is relatively smaller and concentric to the center line of the wave guide 204, thus providing a narrow field of view. The outer sensor 212, on the other hand, is somewhat larger and positioned outside the perimeter of the wave guide, thereby providing a relatively wider field of view.

The temperature sensor may be used in combination with a mechanism that detects the presence of fluid in the middle ear, such as an acoustic reflectometer. The uncorrected temperature or output of two radiation sensors may be used to provide alignment between the device and the tympanic membrane for acoustic reflectance measurements.

With either a fluid detector or temperature sensor, or both, an array of chemical sensors may be used. An array of sensors can be used to analyze the chemical composition of fluids. The fluids may be gaseous in nature. Devices of this type are described in U.S. Pat. Nos. 5,571,401 (Lewis) and 5,5,698,089 (Lewis), assigned to the California Institute of Technology. The sensors are resistors made of alternating conductive and non-conductive materials of which the resistance varies in the presence of specific compounds. The resistors have a different resistance when contacted with a fluid comprising a chemical analyte at a first concentration, than when contacted with a fluid comprising the chemical analyte at a second, different concentration. Leads attached to the sensors are connected to an electrical measuring device. The device measures changes in resistivity at each sensor of the array over time. The signal from the chemical sensors may be processed using principle component analysis and compared to sensed patterns of known bacteria or viruses to determine the presence of a bacterium or virus. An array of chemical sensors may be implemented in many ways to provide signals to the microprocessor controller. An analysis of a characteristic, such as bacterial or viral content, of fluid behind the middle of the ear then may be performed by the microprocessor or other computer.

Figure 8:
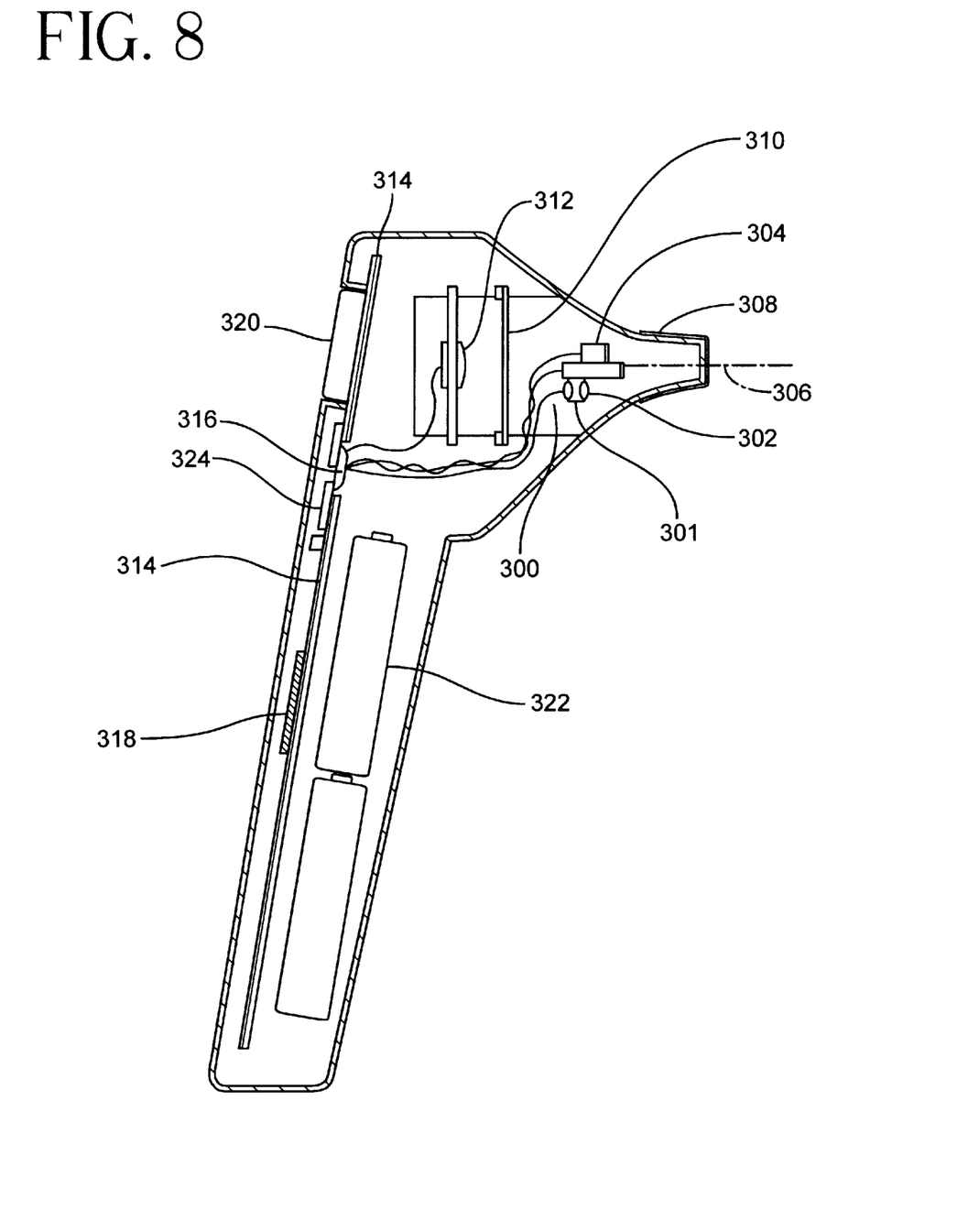
FIG. 8 is a diagram illustrating the physical layout of the array of chemical sensors, microphone of the acoustic reflectometer, and the temperature sensor within an acoustic chamber for the circuit shown in FIG. 1.

The physical arrangement of the microphone, temperature sensor, and array of chemical sensors within an acoustic chamber in a device such as shown in FIG. 1 will now be described in more detail in connection with FIG. 8. FIG. 8 shows a cross section of the device. The device includes an acoustic chamber 300 in which a temperature sensor 302, array of chemical sensors 301, and microphone 304 are disposed. The temperature sensor 302 is aligned with an axis 306 through the tip 308 of the device. An acoustic resistor 310 and speaker 312 generate the acoustic waves out of the device. The device also includes a printed circuit board 314 which includes analog circuitry 316 for processing and controlling the speaker, microphone, array of chemical sensors, and temperature sensor. The device may be powered by batteries 322. A microprocessor 318 is used to process these results and generate output to a user using the LCD display 320, in response to the user pressing an input button 324. Suitable designs for the LCD display include a display of temperature, a measure of the likelihood of fluid being present in the ear and/or a characteristic of the fluid, such as described in the patents cited above. The device may be calibrated in the manner described in U.S. Pat. No. 5,699,809. The device also may have an output to a computer which may perform an analysis give the measurements or an input for receiving temperature and chemical analysis information.

Figure 9:
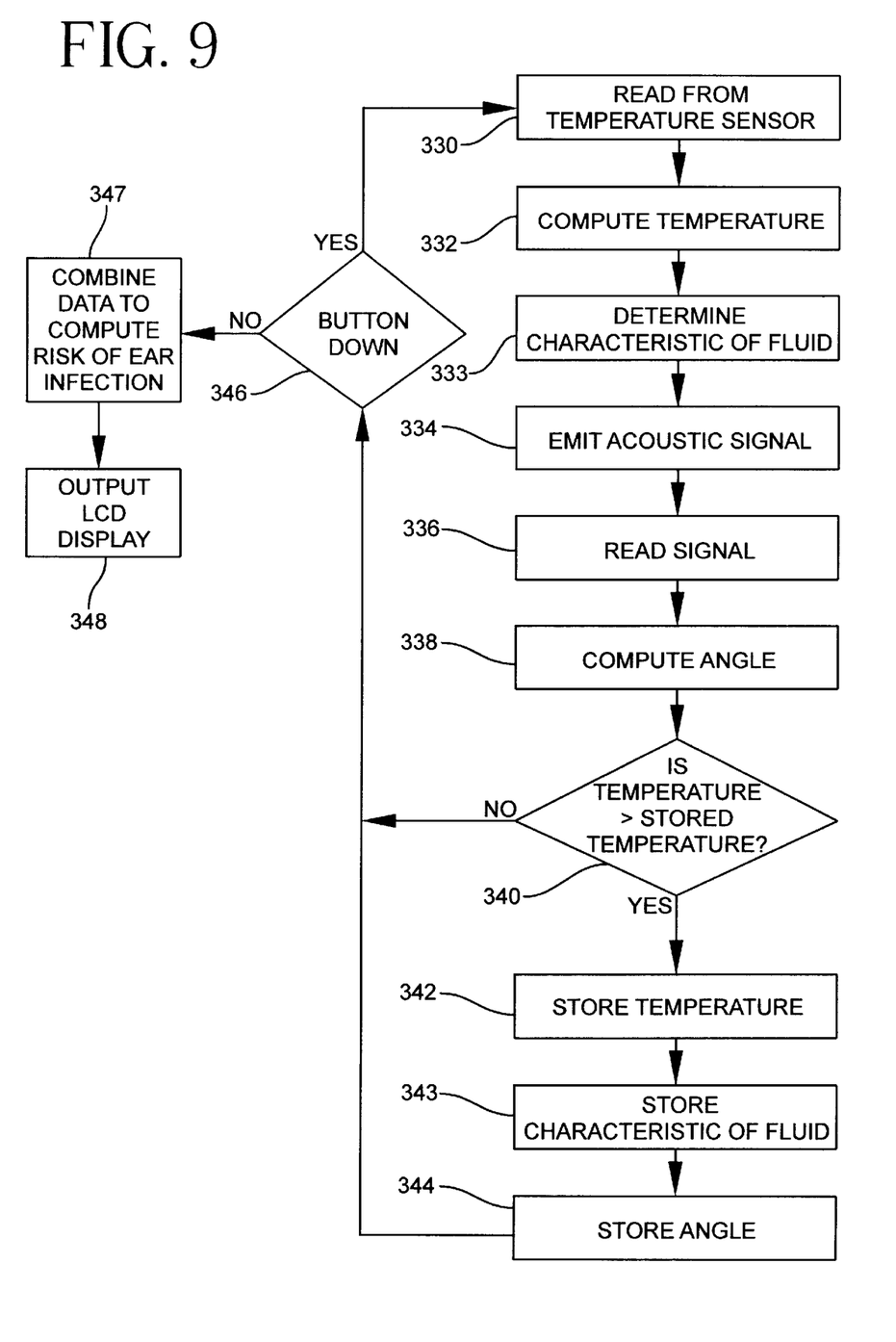
FIG. 9 is a flow chart describing how readings from the array of chemical sensors, temperature sensor, and microphone for the device in FIGS. 1 and 8 are coordinated to provide an output to a user.

FIG. 9 is a flow chart describing how the microprocessor controller 38 (FIG. 1) coordinates the reading of information from the microphone, array of chemical sensors, and temperature sensor to provide an output to the user. So long as the user is providing an input signal indicating a reading should be taken, for example by pressing the input button, data from the temperature sensor is read in step 330. The user should rotate the device with the tip against the opening to the ear canal while pressing the button. Any lobe of the ear also may be pulled lightly back to help align the device. An uncorrected temperature is then computed from the temperature sensor data using known techniques in step 332. A characteristic of the fluid, such as its bacterial and viral content, is then computed from the chemical sensor data using known techniques in step 333. The acoustic signal is also emitted in step 334 and a signal is read from the microphone in step 336. A measure of the likelihood of the presence of fluid is then determined in step 338. For example, this measure may be determined by computing the measure of the shape of the acoustic reflectance curve, or by measuring the peak of the acoustic reflectance curve. If the temperature computed in step 332 is greater than any stored temperature, as determined in step 340, the currently measured temperature is stored in step 342, determined characteristic of the fluid is stored in step 343, and the computed acoustic reflectance measure also is stored in step 344. Alternatively, in step 340, a minimized angle or peak value may be used. If, in step 340, an acoustic reflectance measurement is used, steps 330 to 333 may be performed after step 340. If, in step 340, a temperature measurement is used, steps 330 to 338 may be performed after step 340. If the user input signal still indicates a reading should be taken, as determined in step 346, the process of steps 330–344 is repeated. Otherwise, a measure of the likelihood of the presence of a middle ear infection is then determined in step 347. The resulting output is provided to the LCD display in step 348, possibly providing a corrected temperature as shown in U.S. Pat. No. 5,626,147.

The combination of an array of chemical sensors, a temperature sensor, and fluid detector provides enhanced diagnostic utility. The determination of the presence or absence of an abnormal temperature in conjunction with the determination of the likelihood of presence of fluid that is infected may assist a physician in the diagnosis of an acute otitis media with an effusion. In particular, an elevated temperature and the presence of fluid containing bacteria and viruses indicate a high risk of ear infection. Using radiation thermometry to sense temperature in the ear and acoustic reflectance to detect fluid, the line of sight to the tympanic membrane may be improved which in turn improves measurements of acoustic reflectance.

The measured temperature, the measure related to the likelihood that fluid is present in the ear, and the measures related to the characteristic of the fluid may be displayed separately and/or may be combined to provide an additional diagnostic measure. This diagnostic measure may be computed in many ways, such as a look up table or formula that maps ranges of bacterial and viral content, temperature, and acoustic reflectance to the likelihood that an ear infection is present.

There are numerous display formats ranging from quantitative numerical readings to ranges of risk level. For example, quantitative readings shown in FIGS. 10, 11, and 12, and the ranges of risk level shown in FIGS. 13 through 18A–B may be displayed to a user, as described below. Alternatively, the absolute values of temperature and likelihood of presence of fluid in the ear, and the bacterial and viral content also could be displayed to the user.

Figure 10:
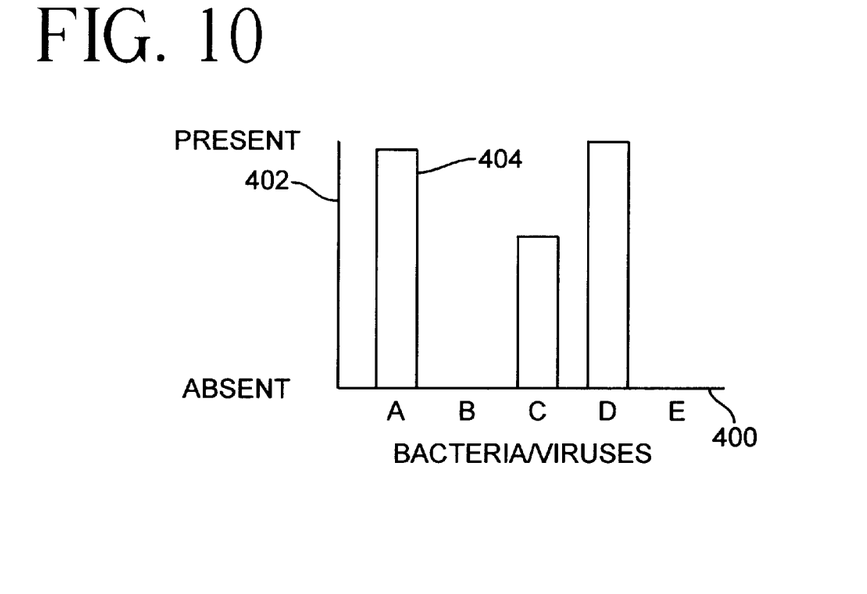
FIG. 10 is an example output of the readings determined by a device that performs chemical sensing of a characteristic of a fluid.

Referring now to FIG. 10, where the characteristic of the fluid is the presence of a bacterium and/or a virus, the presence of the bacterium or virus may be displayed by a bar chart. On the horizontal axis 400 an indicator for each bacterium or virus is shown. On the vertical axis of 402, a range of values indicating the presence or absence of the bacterium or virus is provided. Associated with each bacterium or virus is a value, e.g., 404, indicating the likelihood of presence of that bacterium in any fluid in the ear.

Figure 11:
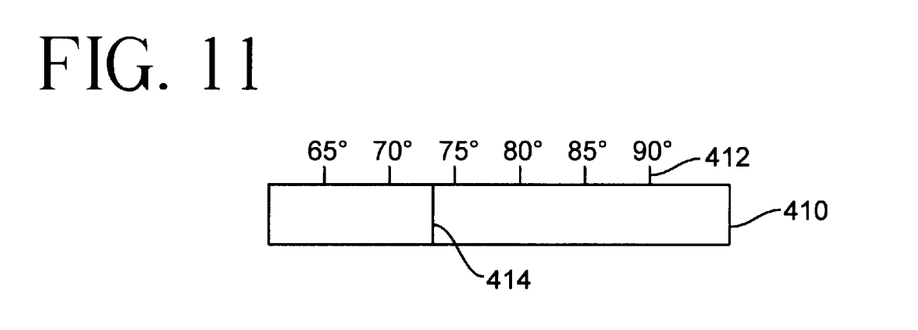
FIG. 11 is an example output of the readings determined by a device that measures acoustic reflectance.

Referring now to FIG. 11, a measure of likelihood that fluid is present in the ear, such as a spectral gradient angle from an acoustic reflectance measurement, may be displayed using a bar 410 demarcations 412, each of which is associated with the measure, such as an angle. A line 414 is displayed on the bar 410 to indicate the computed measure.

Figure 12:
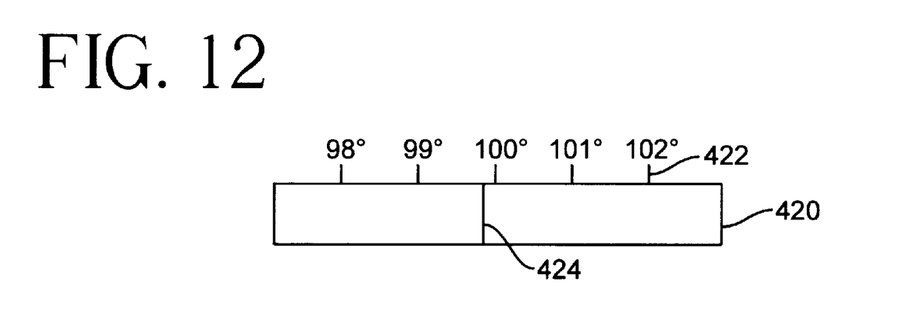
FIG. 12 is an example output of the readings determined by a device that measures temperature.

Referring now to FIG. 12, the temperature may be displayed using a similar scale or bar as shown at 420. Demarcations 422 are provided, each of which is associated with a temperature. A line 424 is displayed on the bar 420 to indicate the measured temperature.

Figure 13:
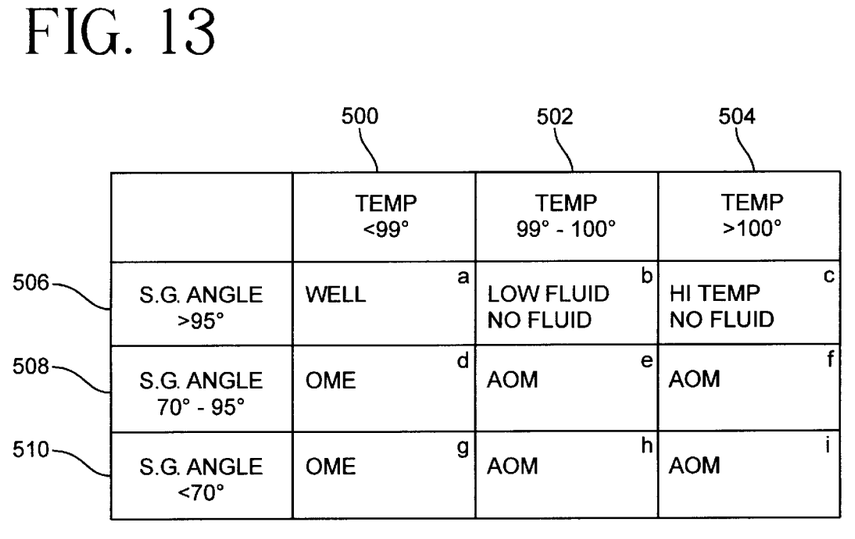
FIG. 13 is an example look-up table for providing a diagnosis based on both temperature and a measure of acoustic reflectance.
Figure 14:
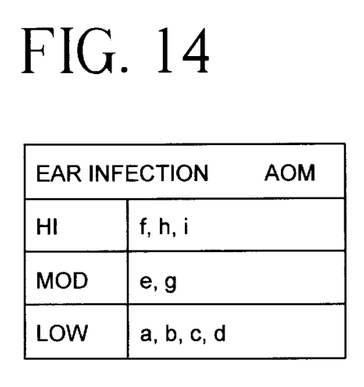
FIG. 14 is an example table for displaying the likelihood of an ear infection based on the results obtained from the look-up table of FIG. 13.
Figure 15:
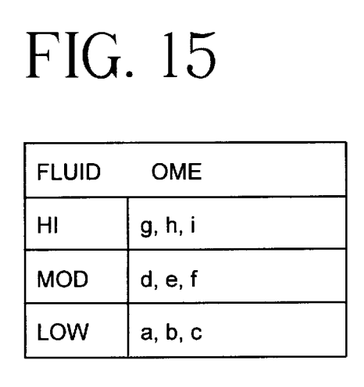
FIG. 15 is an example table for displaying the probability of fluid being present in the middle ear based on the results obtained from the look-up table of FIG. 13.

In the device shown in FIGS. 1 and 8, the device measures temperature and detects the presence of middle ear fluid. The measurements are stored in a memory. Using the temperature and fluid data, the processor then uses a relational formula or a look-up table to determine the probability of ear infection. For example, as shown in FIG. 13, column 500 represents normal temperatures (e.g. <99° F.). Column 502 represents a slightly elevated temperature (e.g. 99° to 100° F.) and column 504 represents an elevated temperature (e.g. >100° F.). Row 506 corresponds to normal acoustic reflectance. Row 508 corresponds to an increased possibility that fluid is present in the ear. Row 510 corresponds to acoustic reflectance which is highly likely to be indicative of the presence of fluid in the ear. As can be seen, an elevated temperature and increased likelihood of fluid being present in the ear very likely indicates acute otitis media, as shown at boxes F, H and I. Box A of the table indicates a healthy ear. The likelihood of ear infection is also low for boxes B, C and D. Otitis media with effusion is highly likely in box G and moderately likely in box D. Acute otitis media is moderately likely in box E. The correspondence of the boxes to the likelihood of ear infection being present is shown in FIG. 14. Similarly, such a table for fluid is shown in FIG. 15. Note that box D corresponds to a low likelihood of ear infection, but moderate likelihood of the presence of fluid. Similarly, while box G indicates a high likelihood of an effusion being present, such a result indicates only a moderate likelihood of an ear infection. Finally, box F, which indicates only a moderate likelihood of fluid being present, indicates a high likelihood of an ear infection being present.

There are numerous display formats ranging from quantitative numerical readings to ranges of risk level. For example, the ranges of risk level shown in FIGS. 14 and 15 could be displayed to a user. Alternatively, the absolute values of temperature and acoustic reflectance also could be displayed to the user.

Figure 16:
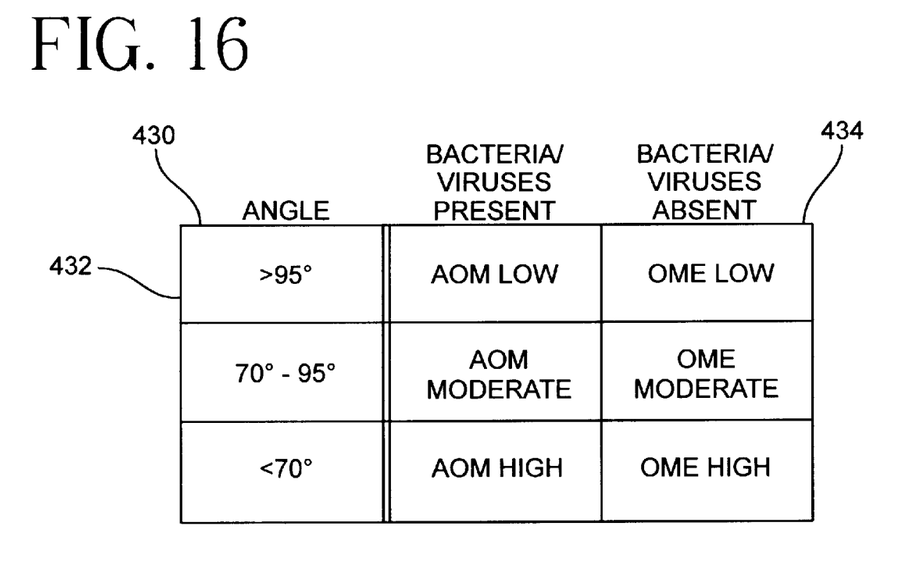
FIG. 16 is an example look-up table for displaying the likelihood of an ear infection based on identification of a characteristic of a fluid and a measure of acoustic reflectance.

FIG. 16 is a table 430 illustrating ranges of risk level, which may be displayed to a user, for a device that combines an array of chemical sensors with acoustic reflectometry. Each row 432 is associated with a range of spectral gradient angles. Each column 434 is associated with the presence or absence of a bacterium or virus.

Figure 17:
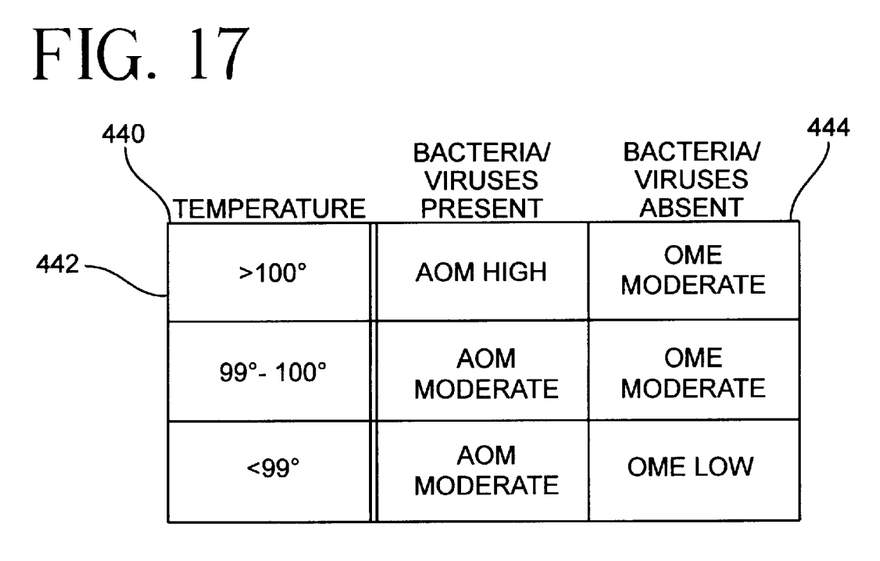
FIG. 17 is an example look-up table for displaying the likelihood of an ear infection based on identification of a characteristic of a fluid and temperature.

Referring now to FIG. 17, a similar table 440 may be displayed to a user for a device that combines an array of chemical sensors with thermometry. In particular, each row 442 is associated with a range of temperatures. Each column 444 is associated with the presence or absence of a bacterium or virus, or if no fluid is present.

Figure 18A:
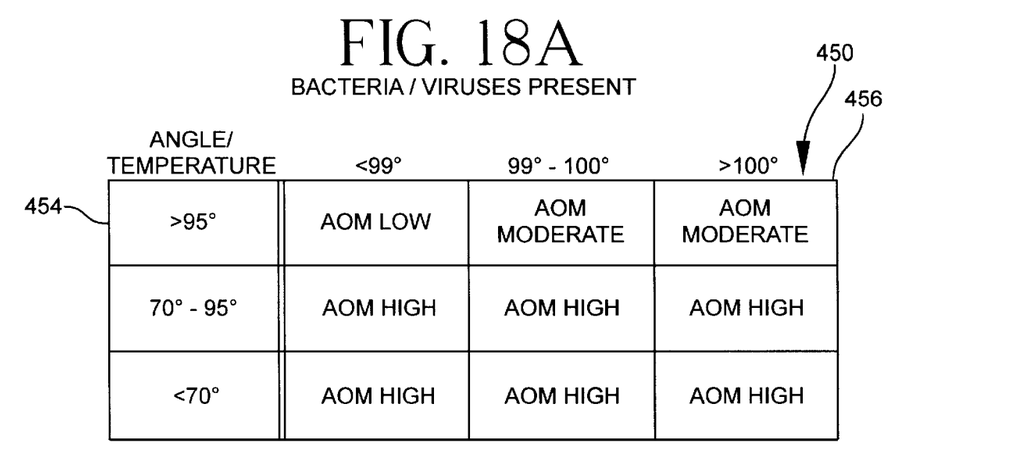
FIGS. 18A and 18B provide an example look-up table for displaying the likelihood of an ear infection based on identification of a characteristic of a fluid, temperature and a measure of acoustic reflectance.
Figure 18B:
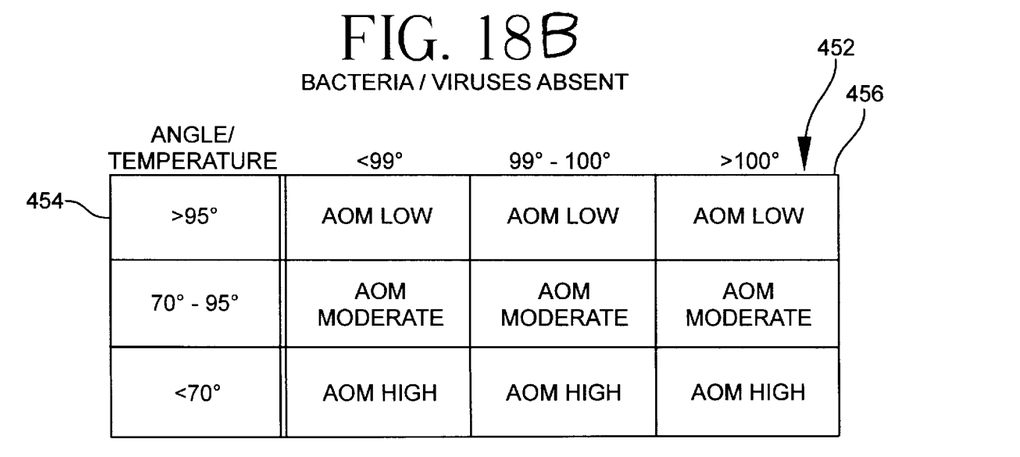

Referring now to FIGS. 18A and 18B, tables 450 and 452 may be displayed as the output of a device that combines an array of chemical sensors with both acoustic reflectometry and thermometry. FIG. 18A is a display shown if a bacterium or a virus is present. FIG. 18B is a display shown if a bacterium or a virus is not present. Each row 454 is associated with a range of spectral gradient angles. Each column 456 is associated with ranges of temperatures. The value in each cell in the tables in FIGS. 16, 17 and 18A–18B indicates the level of risk (either low, moderate or high) of otitis media with effusion (OME) or acute otitis media (AOM). Many other displays may be provided. For example, the determined level of risk may be displayed to the user instead of the table used to obtain the level of risk. Such a display provides an improved diagnostic measure for evaluating the risk of these and other ear pathologies.

Having now described a few embodiments, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention.

What is claimed is:

1. A medical instrument for analyzing an ear of a subject, comprising:
   a temperature sensor for measuring body temperature of the subject and providing a first signal indicative thereof;
   a fluid detector for detecting presence of fluid in the ear to provide a second signal indicative thereof; and
   a controller connected to the temperature sensor and the fluid detector to control acquisition of the first and second signals.

2. The medical instrument of claim 1, further comprising:
   a processor connected to receive the first and second signals for determining, using the measured body temperature and the detected presence of fluid in the ear, an indication of a condition of the ear of the subject.

3. The medical instrument of claim 1, wherein the fluid detector comprises:
   an acoustic transducer for generating acoustic energy in the ear; and
   a microphone for detecting acoustic energy from the ear.

4. The medical instrument of claim 1, wherein the fluid detector is an acoustic reflectometer comprising an acoustic transducer for generating acoustic waves at a plurality of frequencies and a microphone for receiving acoustic signals reflected from the ear to provide an output signal.

5. The medical instrument of claim 1, wherein the temperature sensor is a radiation sensor for detecting thermal radiation from the ear and providing a signal indicative thereof.

6. The medical instrument of claim 1, further comprising:
   means for indicating to the user whether both an elevated temperature and fluid are detected in the ear.

7. The medical instrument of claim 6, wherein the means for indicating includes:
   means for combining temperature and fluid information to provide an indication of a risk of ear infection.

8. The medical instrument of claim 1, further comprising:
   an array of chemical sensors responsive to a characteristic of the fluid to provide a third signal indicative thereof; and
   wherein the controller is further connected to the array of chemical sensors to control acquisition of the third signal.

9. The medical instrument of claim 8, wherein the characteristic of the fluid is the presence of a bacterium in the fluid.

10. The medical instrument of claim 9, further comprising:
    means for indicating to the user whether an elevated temperature and a bacterium are detected in the ear.

11. The medical instrument of claim 9, further comprising:
    means for indicating to the user whether both fluid and a bacterium are detected in the ear.

12. The medical instrument of claim 8, wherein the characteristic of the fluid is the presence of a virus in the fluid.

13. The medical instrument of claim 12, further comprising:
    means for indicating to the user whether an elevated temperature and a virus are detected in the ear.

14. The medical instrument of claim 12, further comprising:
    means for indicating to the user whether both fluid and a virus are detected in the ear.

15. The medical instrument of claim 8, further comprising:
    means for indicating to the user whether an elevated temperature and a negative characteristic of the fluid are detected in the ear.

16. The medical instrument of claim 8, further comprising:
    means for indicating to the user whether both fluid and a negative characteristic of the fluid are detected in the ear.

17. The medical instrument of claim 8, further comprising:
    means for analyzing the first, second and third signals to provide an indication of risk of ear infection according to detected temperature, any detected fluid and any detected characteristic of the fluid.

18. A process for analyzing an ear of a subject, comprising:
    measuring body temperature of the subject and providing a first signal indicative thereof;
    detecting presence of fluid in the ear and providing a second signal indicative thereof; and
    determining, using the measured body temperature and the detected presence of fluid in the ear, an indication of a condition of the ear of the subject.

19. The process of claim 18, wherein the step of detecting fluid includes:
    generating acoustic energy in the ear; and
    detecting acoustic energy from the ear.

20. The process of claim 19, wherein the step of generating acoustic energy includes generating acoustic waves at a plurality of frequencies.

21. The process of claim 18, wherein the step of measuring body temperature includes detecting thermal radiation from the ear and providing a signal indicative thereof.

22. The process of claim 18, further comprising:
    indicating to the user whether both an elevated temperature and fluid are detected in the ear.

23. The process of claim 22, wherein the step of indicating includes combining temperature and fluid information to provide an indication of a risk of ear infection.

24. The process of claim 18, further comprising:
    detecting a characteristic of the fluid to provide a third signal indicative thereof; and
    wherein the step of determining further uses the detected characteristic of the fluid.

25. The process of claim 24, wherein the characteristic of the fluid is the presence of a bacterium in the fluid.

26. The process of claim 25, further comprising:
    indicating to the user whether an elevated temperature and a bacterium are detected in the ear.

27. The process of claim 25, further comprising:
    indicating to the user whether both fluid and a bacterium are detected in the ear.

28. The process of claim 24, wherein the characteristic of the fluid is the presence of a virus in the fluid.

29. The process of claim 28, further comprising:
    indicating to the user whether an elevated temperature and a virus are detected in the ear.

30. The process of claim 28, further comprising:
    indicating to the user whether both fluid and a virus are detected in the ear.

31. The process of claim 24, further comprising:
    indicating to the user whether an elevated temperature and a negative characteristic of the fluid are detected in the ear.

32. The process of claim 24, further comprising:

indicating to the user whether both fluid and a negative characteristic of the fluid are detected in the ear.

33. The process of claim 24, further comprising:

analyzing the first, second and third signals to provide an indication of risk of ear infection according to detected temperature, any detected fluid and any detected characteristic of the fluid.

34. A device for providing an indication of a condition of an ear of a subject, comprising:

a first input for receiving a first signal indicative of a measured body temperature of the subject;

a second input for receiving a second signal indicative of a likelihood of presence of fluid in the ear of the subject; and a processor connected to receive the first and second inputs for determining, using the measured body temperature and the likelihood of presence of fluid in the ear, the indication of the condition of the ear of the subject.

35. The device of claim 34, further comprising:

a third input for receiving a third signal indicative of a determined characteristic of any fluid in the ear of the subject; and wherein the processor is connected to receive the third input and determines the indication of the condition of the ear of the subject further using the determined characteristic of any fluid in the ear of the subject.

36. A medical instrument for analyzing an ear of a subject, comprising:

an array of chemical sensors responsive to a characteristic of any fluid in the ear to provide a first signal indicative thereof; and a fluid detector for detecting presence of fluid in the ear to provide a second signal indicative thereof; and a controller connected to the array of chemical sensors and the fluid detector to control acquisition of the first and second signals.

37. The medical instrument of claim 36, wherein the characteristic of the fluid is the presence of a bacterium in the fluid.

38. The medical instrument of claim 37, further comprising:

means for indicating to the user whether both fluid and a bacterium are detected in the ear.

39. The medical instrument of claim 36, wherein the characteristic of the fluid is the presence of a virus in the fluid.

40. The medical instrument of claim 39, further comprising:

means for indicating to the user whether both fluid and a virus are detected in the ear.

41. The medical instrument of claim 36, further comprising:

means for indicating to the user whether both fluid and a negative characteristic of the fluid are detected in the ear.

42. The medical instrument of claim 36, further comprising:

a processor connected to receive the first and second signals for determining, using the detected presence of fluid in the ear and determined characteristic of the fluid, an indication of a condition of the ear of the subject.

43. The medical instrument of claim 36, wherein the fluid detector comprises:

an acoustic transducer for generating acoustic energy in the ear; and a microphone for detecting acoustic energy from the ear.

44. The medical instrument of claim 36, wherein the fluid detector is an acoustic reflectometer comprising an acoustic transducer for generating acoustic waves at a plurality of frequencies and a microphone for receiving acoustic signals reflected from the ear to provide an output signal.

45. A medical instrument for analyzing an ear of a subject, comprising:

an array of chemical sensors responsive to a characteristic of the fluid to provide a first signal indicative thereof;

a temperature sensor for measuring body temperature of the subject and providing a second signal indicative thereof; and a controller connected to the array of chemical sensors and the temperature sensor to control acquisition of the first and second signals.

46. The medical instrument of claim 45, wherein the characteristic of the fluid is the presence of a bacterium in the fluid.

47. The medical instrument of claim 46, further comprising:

means for indicating to the user whether an elevated temperature and a bacterium are detected in the ear.

48. The medical instrument of claim 45, wherein the characteristic of the fluid is the presence of a virus in the fluid.

49. The medical instrument of claim 48, further comprising:

means for indicating to the user whether an elevated temperature and a virus are detected in the ear.

50. The medical instrument of claim 45, further comprising:

means for indicating to the user whether an elevated temperature and a negative characteristic of the fluid are detected in the ear.

51. The medical instrument of claim 45, further comprising:

a processor connected to receive the first and second signals for determining, using the measured body temperature and the determined characteristic of fluid in the ear, an indication of a condition of the ear of the subject.

52. The medical instrument of claim 45, wherein the temperature sensor is a radiation sensor for detecting thermal radiation from the ear and providing a signal indicative thereof.

* * * * *